United States Patent [19]
Hsia

[11] Patent Number: 5,811,005
[45] Date of Patent: Sep. 22, 1998

[54] APPARATUS FOR INTRAVENOUS ADMINISTRATION OF SOLUTIONS OF CELL-FREE HEMOGLOBIN INCLUDING A NITROXIDE BOUND TO A MATRIX

[76] Inventor: Jen-Chang Hsia, 135 Starcrest, Irvine, Calif. 92715

[21] Appl. No.: 541,228

[22] Filed: Oct. 12, 1995

Related U.S. Application Data

[63] Continuation of Ser. No. 107,543, Aug. 16, 1993, abandoned.

[51] Int. Cl.$^6$ .......................... B01D 15/08; B01D 29/05
[52] U.S. Cl. ...................... 210/483; 210/198.2; 210/252; 210/496; 422/101; 205/404; 514/315; 514/408
[58] Field of Search ................................. 210/198.2, 252, 210/496, 483, 500, 27; 422/101; 435/174, 177, 178, 179, 182; 514/315, 408; 530/413, 417, 810, 812, 814, 817; 502/404

[56] References Cited

U.S. PATENT DOCUMENTS

| | | |
|---|---|---|
| 3,959,287 | 5/1976 | Goldstein et al. . |
| 4,001,200 | 1/1977 | Bonsen et al. . |
| 4,001,401 | 1/1977 | Bonsen et al. . |
| 4,053,590 | 10/1977 | Bonsen et al. . |
| 4,061,736 | 12/1977 | Morris et al. . |
| 4,136,093 | 1/1979 | Bonhard et al. . |
| 4,301,144 | 11/1981 | Iwashita et al. . |
| 4,336,248 | 6/1982 | Bonhard et al. . |
| 4,376,095 | 3/1983 | Hasegawa ................................. 422/46 |
| 4,377,512 | 3/1983 | Ajisaka et al. . |
| 4,401,652 | 8/1983 | Simmonds et al. . |
| 4,412,989 | 11/1983 | Iwashita et al. . |
| 4,473,494 | 9/1984 | Tye . |
| 4,473,496 | 9/1984 | Scannon . |
| 4,529,719 | 7/1985 | Tye ............................................. 514/6 |
| 4,563,349 | 1/1986 | Miyata et al. . |
| 4,584,130 | 4/1986 | Bucci et al. . |
| 4,598,064 | 7/1986 | Walder ...................................... 514/6 |

(List continued on next page.)

FOREIGN PATENT DOCUMENTS

| | | |
|---|---|---|
| 0255443 | 2/1988 | European Pat. Off. . |
| 0 290 252 | 11/1988 | European Pat. Off. . |
| 0327263 B1 | 9/1994 | European Pat. Off. . |
| WO84/04248 | 11/1984 | WIPO . |
| WO91/13619 | 9/1991 | WIPO . |

OTHER PUBLICATIONS

"Pharmacokinetic Studies in the Rat on a O–Raffinose Polymerized Human Hemoglobin"; Hsia, J.C. et al., *Biomaterials Artificial Cells and Immobilization Biotechnology*, 1992, V20, N2–4, P587–595.

"Molecular–Weight Determinations of O–Raffinose–Polymerized Human Hemoglobin"; Moore, G. L. et al., *Biomaterials Artificial Cells and Immobilization Biotechnology*, 1992, et al. V20, N2–4, P293–296.

"The Toxicity of Hemoglobin"; R.M. Winslow Edited, *Hemoglobin–Based Red Blood Cell Substitutes*, John Hopkins University Press, Baltimore, 1992, P136–163.

"Quality–Control of Hemoglobin–Based Blood Substitutes"; Hsia, J.C. et al., *Biomaterials Artificial Cells and Artificial Organs*, 1988, V16, N1–3, P105–111.

"Hemoglobin–Based Blood Substitutes: Characterization of Five Pyridoxal 5'–Phosphate Derivatives of Hemoglobin"; McGarrity, M.J. et al., *Journal of Chromatography–Biomedical Applications*, 1987, V419, P37–50.

(List continued on next page.)

*Primary Examiner*—John Kim
*Attorney, Agent, or Firm*—Lyon & Lyon LLP

[57] ABSTRACT

An apparatus for intravenous administration of solutions of cell-free hemoglobin is disclosed. The apparatus includes a solution of cell-free hemoglobin in fluid connection with a housing having an inlet and an outlet through which the solution of cell-free hemoglobin flows and a nitroxide bound to a matrix is contained within the housing to alleviate oxygen toxicity to the cell-free hemoglobins.

7 Claims, 7 Drawing Sheets

U.S. PATENT DOCUMENTS

| | | |
|---|---|---|
| 4,600,531 | 7/1986 | Walder ......................................... 514/6 |
| 4,670,417 | 6/1987 | Iwasaki et al. .............................. 514/6 |
| 4,780,210 | 10/1988 | Hsia ........................................ 210/638 |
| 4,822,681 | 4/1989 | Schössler et al. .................... 210/198.2 |
| 4,826,811 | 5/1989 | Sehgal et al. ................................ 514/6 |
| 4,831,012 | 5/1989 | Estep ........................................... 514/6 |
| 4,834,964 | 5/1989 | Rosen .......................................... 424/9 |
| 4,857,636 | 8/1989 | Hsia ............................................. 514/6 |
| 4,863,717 | 9/1989 | Keana .......................................... 424/9 |
| 4,873,191 | 10/1989 | Wagner et al. ....................... 435/172.3 |
| 4,911,929 | 3/1990 | Farmer et al. ........................... 424/450 |
| 4,920,194 | 4/1990 | Feller et al. ................................. 514/6 |
| 4,925,574 | 5/1990 | Hsia ......................................... 210/635 |
| 4,959,305 | 9/1990 | Woodrum .................................... 435/7 |
| 5,061,688 | 10/1991 | Beissinger et al. ......................... 514/6 |
| 5,080,645 | 1/1992 | Hanig .......................................... 604/4 |
| 5,104,641 | 4/1992 | Rosen .......................................... 424/9 |
| 5,114,932 | 5/1992 | Runge ......................................... 514/6 |
| 5,149,425 | 9/1992 | Mazid ................................. 210/198.2 |
| 5,234,903 | 8/1993 | Nho et al. .................................... 514/6 |

OTHER PUBLICATIONS

"Quality–Control and Scale–Up Production of Hemoglobin–Based Substitutes—From High–Pressure Liquid Chromatography to Tangential Flow Affinity Ultafiltration"; Hsia, J. C., *Biomaterials, Artificial Cells, and Artificial Organs*, 1987, V15, N2, P364.

"Reduced Coronary Vasoconstrictor Activity of Hemoglobin Solutions Purified by ATP–Agarose affinity Chromatography"; Vogel, W.M. et al., *Life Sciences*, 1987, V41, N1, P89–93.

"ATP–Hemoglobin: Anomalous Oxygen Binding Properties"; McGarrity, M.J. et al., *Journal of Chromatography–Biomedical Applications*, 1987, V415, N1, P136–142.

"Isolation and Partial Characterization of Pyridoxal 5'–Phosphate Hemoglobins by High–Performance Liquid Chromatography as a Quality–Control Method for Hemoglobin–Based Blood Substitutes"; M.J. McGarrity et al., *Journal of Chromatography–Biomedical Applications*, 1987, V413, Jan. P53–63.

"ATP–Hemoglobin Purfication by ATP–Agarose Affinity Chromatography"; J.C. Hsia et al., *Journal of Chromatography*, 1986, v381, N1, P153–157.

"Cell–Free Hemoglobin Potentiates Acetylcholine–Induced Coronary Vasoconstriction in Rabbit Hearts"; R. Motterlini et al., *Journal of Applied Physiology*, 1993 V75, P2224–2233.

"Consequences of Chemical Modifications on the Free Radical Reactions of Human Hemoglobin"; A.I. Alayash et al., *Archives of Biochemistry and Biophysics*, 1992, V289, N1, Oct. P114–120.

"Biologically Active Metal–Independent Superoxide Dismutase Mimics"; JB Mitchell et al., *Biochemistry*, 1990, V29, P2802–2807.

"Purification of Stroma–Free Haemoglobin by ATP–Agarose Affinity Chromatography"; J.C. Hsia et al., *Journal of Chromatography*, 1986, V374, N1, P143–148.

"Superoxide Reaction with Nitroxides"; A. Samuni et al., *Free Rad. Res Comms.*, 1990, V9, P241–249.

"Nitroxide–stimulated $H_2O_2$ Decomposition by Peroxidases and Pseudoperoxidases"; R.J. Mehlhorn et al., *Free Rad. Res. Comms.*, 1992, v17, N3, P157–175.

"Fine Tuning of Polymerized Pyridoxylated Hemoglobin as a Red Blood Cell Substitute"; J.C. Hsia, *The Red cell: Seventh Ann Arbor Conference*, 1989, P339–349.

"A Clinical Safety Trial of Stroma–Free Hemoglobin"; J.P. Savitsky et al., *Clin. Pharmacol. Ther.*, 1978, V23, P73–80.

"Perspectives on Hydrogen Peroxide and Drug–Induced Hemolytic Anemia in Glucose–6–Phosphate Dehydrogenase Deficiency," P. Hochestein, *Free Radical Biology & Medicine*, 1988, V5, P387–392.

"Pharmacological Evidence that Endothelium–Derived Relaxing Factor is Nitric Oxide: Use of Pyrogallol and Superoxide Dismutase to Study Endothelium–Dependent and Nitric Oxide–Elixited Vascular Smooth Muscle Relaxation", L.J. Ignarro et al., *Journal of Pharmacology and Experimental Therapeutics*, 1988, v244, N1, P181–189.

"Superoxide Anions and Hyperoxia Inactivate Endothelium–Derived Relaxing Facor," G. M. Rubanyi et al., *American Journal of Physiology*, (1986), (Heart Cir. Physiol. 19): V250, PH822–H827.

"Superoxide Anion is Involved in the Breakdown of Endothelium–Derived Vascular Relaxing Factor," R. J. Gryglewski et al., *Nature*, (1986). V320, P454–456.

"Biosynthesis and Metabolism of Endothelium–Derived Nitric Oxide," Louis J. Ignarro, *Annu. Rev. Pharmacol. Toxicol.*, (1990), v30, P535–560.

"Characterization of the L–Arginine:Nitric Oxide Pathway in Human Platelets," M. W. Radomski et al., *Br. J. Pharmacol*, (1990), V101, P325–328.

"Selective Blockade of Endothelium–Dependent and Glyceryl Trinitrate–Induced Relaxation by Hemoglobin and by Methylene Blue in the Rabbit Aorta," William Martin et al., *The Journal of Pharmacology and Experimental Therapeutics*, (1985), V232, N3, P708–716.

"Electron Spin Echo Studies of Hemoglobin Cyanide and Nitroxide Derivatives"; Y.V.S. Rama Krishna et al., *Biochimica et Biophysica Acta*, 1987, V916, P48–53.

"Physics and Chemistry of Spin Labels," H.M. McConnell, et al., *Quarterly Reviews of Biophysics*, 1970, v3, N1, P91–136.

"Spin Labels"; C. Hamilton et al., *Structural Chemistry and Molecular Biology*, A. Rich et al, eds. W. H. Freeman, San Francisco, 1968, P115–149.

"Nitroxide Free Radicals: Spin Labels for Probing Biomolecular Structure," O.H. Griffith et al., *Accounts of Chemical Research*, 1969, V2, N1, P17–24.

"The Spin Label Method"; I.C.P. Smith, *Biological Applications of Electron Spin Resonance*, H.M. Swartz, et al., eds., Wiley/Interscience, New York, 1972 P484–539.

"Relaxation of Bovine Coronary Artery and Activation of Coronary Arterial Guanylate Cyclase by Nitric Oxide, Nitroprusside and a Carcinogenic Nitrosamine," C.A. Grueter et al., *Journal of Cyclic Nucleotide Research*, 1979, V5, N3 P211–224.

"Detection of Free Radicals as Intermediates in the Methemoglobin Formation from Oxyhemoglobin Induced by Hydroxylamine"; Klaus Stolze et al., *Biochemical Pharmacology*, 1989, V38, N18, P3055–3059.

"Nitroxide–Stimulated $H_2O_2$ Decomposition by Peroxidases and Pseudoperoxidases"; Rolf J. Mehlhorn and Christopher E. Swanson. Free Rad. Res. Comms. V17, N3, P157–175.

"Nitric Oxide, and Inhibitor of Lipid Oxidation by Lipoxygenase, Cycloosygenase, and Hemoglobin"; Joseph Kanner, Stela Harel, and Rina Granit Lipids, 1992, V27, N1, P46–49.

"Inhibition of Lipid Peroxidation by Spin Labels—Relationships Between structure and Function"; Ulf A. Nilsson, Lars–Inge Olsson, Gunnar Carlin, and Ann–Christin Bylund–Fellenius the Journal of Biological Chemistry, 1989, V264, P11131–11135 (1989).

"Preservation of Metabolic Activity in Lyophilized Human Erythrocytes"; R. Goodrich, et al., *Proc. Natl. Acad. Sci. USA,* V89, P967–971 (1992).

"Nitroxides as Protectors Against Oxidative Stress"; James B. Mitchell and Angleo Russo Presented at New developments in free radical research: Prospects for New Drugs Jun. 27–28, 1991, Philadelphia, PA. Sponsored by International Business Communiations.

"Superoxide Reaction with Nitroxides"; Amram Samuni, C. Murali Krishna, James B. Mitchell, Christi R. Collins, and Angelo Russo Free Rad. Res. Comms., 1990, v9, P241–249.

"Sterically–Hindered hydroxylamines as Bioactive Spin Labels"; Renat I. Zhdanov, and Pavel G. Komarov Free Rad. Res. Comms, 1990, V9, P367–377.

"SOD–Like activity of 5–Membered Ring Nitroxide Spin Labels"; Amram Samuni, Ahn Min, C. Murali Krishna, James B. Mitchell, and Angelo Russo. Antioxidants in Therapy and Preventive Medicine, 1990, P85–92.

"Biologically Active Metal–Independent Superoxide Dismutase Mimics"; James B. Mitchell, Amram Samuni, Murali C. Krishna, William G. DeGraff, Min S. Ahn, Ur Samuni, and Angelo Russo Biochemistry, 1990, v29, P2802–2807.

"Cardiac Reperfusion Damage Prevented by a Nitroxide Free Radical"; Dan Gelvan, Paul Saltman, and Saul R. Powell Proc. Natl. Acad. Sci., 1991, V88, P4680–4684.

"Nitroxide Block DNA Scission and Protect Cells from Oxidative Damage"; Amram Samuni, Dina Godinger, Jacob Aronovitch, Angelo Russo, and James B. Mitchell Biochemistry, 1991, V30, P555–561.

"Nitroxide Stable Radicals Protect Beating Cardiomyocytes Against Oxidative Damage"; Amram Samuni, Dorit Winkelsberg, Arie Pinson, Stephen M. Hahn, James B. Mitchell, and Angelo Russo The Journal of Clinical Investigation, Inc., 1991, V87, P1526–1530.

"Detection of Myoglobin–Derived Radicals on Reaction of Metmyoglobin with Hydrogen Peroxide and other Peroxidic Compounds"; Michael J. Davies (1990) Free Rad. Res. Comms., 1990, V10, N6, P361–370.

"Perspectives on Hydrogen Peroxide and Drug–Induced Hemolytic Anemia in Glucose–6–Phosphate Dehydrogenase Deficiency"; Paul Hochstein Free Radical Biology & Medicine, 1988, V5, P387–392.

"Mechanisms and Consequences of Lipid Peroxidation in Biological Systems"; Alex Sevanian and Paul Hochstein Ann. Rev. Nutr., 1985, V5, P365–390.

"Uric Acid Provides an Antioxidant Defense in Humans Against Oxidant–and Radical–Caused Aging and Cancer; A Hypothesis"; Bruce N. Ames, Richard Cathcart, Elizabeth Schwiers, and Paul Hochstein Proc. Natl. Acad. Sci. USA, 1981, V78, N11, P6858–6862.

"In Vivo Rat Hemoglobin Thiyl Free Radical Formation Following Phenylhydrazine Administration"; Kirk R. Maples, Sandra J. Jordan, and Ronald P. Mason Molecular Pharmacology, 1988, V33, P344–350.

"Autoxidation of Oxymyoglobin—An Overall Stoichiometry Including Subsequent Side Reactions"; Gen–ichi Tajima and Keiji Shikama The Journal of Biological Chemistry, 1987, v262, P12603–12606.

"A Novel Antioxidant Role for Hemoglobin —The Comproportionation of Ferrylhemoglobin with Oxyhemoglobin"; Cecilia Giulivi and Kelvin J.A. Davies The Journal of Biological Chemistry, 1990, V265, P19456–19460.

"The Reactivity of Thiols and Disulfides with Different Redox States of Myoglobin —Redox and Addition Reactions and Formation of Thiyl Radical Intermediates"; Francisco J. Romero, Ishmael Ordonez, Arduino Arduini, and Enrique Cadenas The Journal of Biological Chemistry, 1992, V267, P1680–1688.

"The Special Role of Myoglobin in Cardiac Ischemia–Reprefusion Injury"; Paul Hochstein and Arduino Arduini Symposium on Biological Free Radicals, Udine, Italy, Jul. 1–5 (1991).

A Protective role for Ascorbate in Induced Ischemic Arrest Associated with Cardiopulmonary Bypass; Lynne Eddy, Richard Hurvitz, and Paul Hochstein *Journal of Applied Cardiology,* 1990, V5, P409–411.

"Pulse Radiolysis Study on the Reactivity of Trolox C. Phenoxyl Radical with Superoxide Anion"; Enrique Cadenas, Gabor Merenyi, and Johan Lind FEBS Letters, 1989, V253, N1–2, P235–238.

"Reversible Conversion of Nitroxyl Anion to Nitric Oxide by Superoxide Dismutase"; Michael E. Murphy and Helmut Sies *Proc. Natl. Acad. Sci. USA,* 1991, V88, P10860–10864.

"A Human Recombinant Haemoglobin Designed for Use as a Blood Substitute"; Douglas Looker, Debbie Abbott–Brown, Paul Cozart Steven Durfee, Stephen Hoffman, Anthony J. Matthews, Jeanne Miller–Roehrich, Steven Shoemaker, Stephen Trimble, Giuilio Fermi, Noboru H. Komiyama, Kiyoshi Nagai, and Gary L. Stetler *Narure,* 1992, V356, P258–260.

"Review Article—Mechanisms of Cardiovascular Drugs as Antioxidants" *J. Mol Cell Cardiol,* 1990, V22, P1199–1208.

"Biochemistry of Oxygen Toxicity"; Enrique Cadenas Annu. Rev. Biochem., 1989, V58, P79–110.

"A Novel Metal–Free Low Molecular Weight Superoxide Dismutase Mimic"; Amram Samuni, C. Murali Krishna, Peter Riesz, Eli Finkelstein, and Angelo Russo The Journal of Biological Chemistry, 1988, V263, P17921–17924.

"Nitroxide Sod–Mimics; Mode of Action," Amram Samuni, James B. Mitchell, William DeGraff, C. Murali Krishna, Uri Samuni, and Angelo Russo Free Rad. Res. Comms. vols. 12–13, pp. 187–194 (1991).

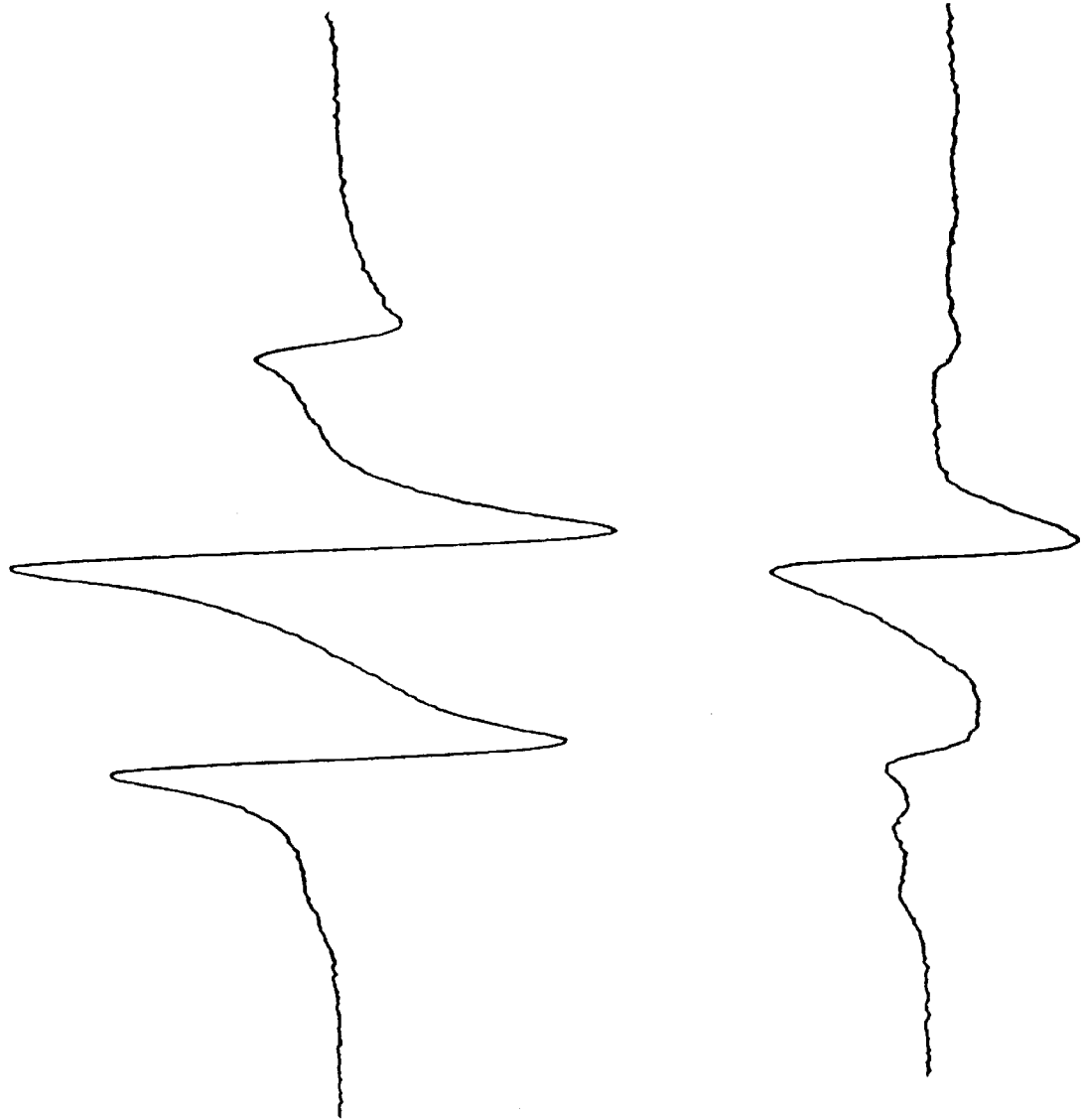

APPARATUS FOR INTRAVENOUS ADMINISTRATION OF SOLUTIONS OF CELL-FREE HEMOGLOBIN INCLUDING A NITROXIDE BOUND TO A MATRIX

This is a continuation of application Ser. No. 08/107,543, filed on Aug. 16, 1993, now abandoned.

FIELD OF THE INVENTION

This invention relates to the use of nitroxide compounds that are used with hemoglobin and with liposomes to alleviate the toxic effects of oxygen-related species in a living organism. In particular, this invention discloses compounds and methods featuring nitroxides associated with physiologically compatible cell-free and encapsulated hemoglobin solutions for use as a red cell substitute.

BACKGROUND OF THE INVENTION

Scientists and physicians have struggled for decades to produce a blood substitute that could be safely transfused into humans. Persistent blood shortages and the problems of incompatible blood types, cross-matching, and the communication of disease have led to a broad-based effort by private industry, universities, and governments to discover a formulation that would allow a large volume of a blood substitute to be safely transfused without significant physiological side effects. At present, several companies are conducting clinical trials on experimental blood substitutes. However, unexpected adverse physiological reactions and the inherent complexity of the research and development process have impeded progress through the regulatory approval stage and have prevented the introduction of a clinically useful blood substitute.

A Research Advisory Committee of the United States Navy issued a report in August 1992 outlining the efforts by several groups to produce a blood substitute, assessing the status of those efforts, and generally describing the toxicity problems encountered. The Naval Research Advisory Committee Report reflects the current consensus in the scientific community that even though the existing blood substitute products, often termed "hemoglobin-based oxygen carriers" (HBOC), have demonstrated efficacy in oxygen transport, certain toxicity issues are unresolved. The adverse transfusion reactions that have been observed in clinical studies of existing hemoglobin-based oxygen carriers (HBOC) include systemic hypertension and vasoconstriction. These adverse reactions have forced a number of pharmaceutical companies to proceed with Phase I clinical trials at very low dosage levels.

The toxicity problem in the existing hemoglobin-based blood substitutes has been given a high priority by the United States Government. The Naval Research Committee recommendation has been implemented by the National Institute of Health in the form of a Request For Proposal (PA-93-23) on the subject of "Hemoglobin-Based Oxygen Carriers: Mechanism of Toxicity." Therefore, the medical and scientific community suffers from an acute and pressing need for a blood substitute that may be infused without the side effects observed with the existing hemoglobin-based oxygen carriers.

The red blood cells are the major component of blood and contain the body's oxygen transport system. It has long been recognized that the most important characteristic of a blood substitute is the ability to carry oxygen. The red blood cells are able to carry oxygen because the primary component of the red cells is hemoglobin, which functions as the oxygen carrier. Most of the products undergoing clinical testing as blood substitutes contain hemoglobin that has been separated from the red blood cell membranes and the remaining constituents of the red blood cells and purified to remove essentially all contaminants. However, when hemoglobin is removed from the red cells and placed in solution in its native form, it is unstable and rapidly dissociates into its constituent subunits. For this reason, the hemoglobin used in a hemoglobin-based oxygen carrier must be stabilized to prevent dissociation in solution. Substantial expenditures in scientific labor and capital were necessary to develop products of hemoglobin that are stable in solution, and are stabilized in such a way that the oxygen transport function is not impaired. The ability of the existing hemoglobin-based blood substitutes to transport oxygen has been well established (See U.S. Pat. Nos. 3,925,344; 4,001,200; 4,001,401; 4,053,590; 4,061,736; 4,136,093; 4,301,144; 4,336,248; 4,376,095; 4,377,512; 4,401,652; 4,473,494; 4,473,496; 4,600,531; 4,584,130; 4,857,636; 4,826,811; 4,911,929 and 5,061,688).

In the body, hemoglobin in the red cells binds oxygen molecules as the blood passes through the lungs and delivers the oxygen molecules throughout the body to meet the demands of the body's normal metabolic function. However, the atmospheric oxygen that most living beings must breathe to survive is a scientific and medical paradox. On the one hand, almost all living organisms require oxygen for life. On the other hand, a variety of toxic oxygen-related chemical species are produced during normal oxygen metabolism. In the process of transporting oxygen, the hemoglobin (Hb) molecule can itself be oxidized by the oxygen ($O_2$) molecule it is carrying. This auto-oxidation reaction produces two undesirable products: met-hemoglobin (met-Hb) and the superoxide anion ($.O_2^-$). The chemical reaction may be written as follows:

$$Hb + 4\ O_2 \rightarrow met\text{-}Hb + 4\ .O_2^- \quad [1]$$

The superoxide anion ($.O_2^-$) is an oxygen molecule that carries an additional electron and a negative charge. The superoxide anion is highly reactive and toxic. Potentially damaging oxidative stress originates with the superoxide anion being generated by the auto-oxidation of hemoglobin and results from the subsequent conversion of the superoxide anion to toxic hydrogen peroxide in the presence of the enzyme superoxide dismutase (SOD) by the following reaction:

$$2\ .O_2^- + 2H^+ \rightarrow 2\ O_2 + H_2O_2 \quad [2]$$

The presence of the superoxide anion and hydrogen peroxide in the red blood cells is believed to be the major source of oxidative stress to the red cells.

Apart from oxygen transport by hemoglobin, a less recognized characteristic of the red cells is that they contain a specific set of enzymes which are capable of detoxifying oxygen-related chemical species produced as by-products of oxygen metabolism. Without the protection of these specific enzyme systems, autoxidation of hemoglobin would lead to deterioration and destruction of the red cells. In the body, however, the reserve capacity of the enzyme systems in the red cells protects the body from oxygen toxicity by converting the superoxide anion generated during normal metabolism to non-toxic species and thereby controls the level of oxidative stress. However, if this enzyme system breaks down, the integrity of the red cells will be damaged. A lesion of the gene that produces one of the enzymes in the protective system in the red blood cells will cause an observable pathological condition. For example, glucose-6-phosphate dehydrogenase deficiency, a genetic disorder of red cells, is responsible for hydrogen peroxide induced hemolytic anemia. This disorder is due to the inability of the affected cells to maintain NAD(P)H levels sufficient for the reduction of oxidized glutathione resulting in inadequate detoxification of hydrogen peroxide through glutathione peroxidase (P. Hochestein, Free Radical Biology & Medicine, 5:387 (1988)).

The protective enzyme system of the red blood cells converts the toxic superoxide anion molecule to a non-toxic form in a two-step chemical pathway. The first step of the pathway is the conversion of the superoxide anion to hydrogen peroxide by the enzyme superoxide dismutase (SOD) (See Equation [2]). Because hydrogen peroxide is also toxic to cells, the red cells contain another enzyme, catalase, which converts hydrogen peroxide to water as the second step of the pathway (See Equation [3]).

$$2\ H_2O_2 \rightarrow 2\ H_2O + O_2 \quad [3]$$

Red cells are also capable of detoxifying hydrogen peroxide and other toxic organoperoxides using the enzyme glutathione peroxidase which reacts with glutathione to convert hydrogen peroxide and organoperoxides to water. Red cells also contain an enzyme to prevent the build up of the met-hemoglobin produced by the auto-oxidation of hemoglobin. The enzyme met-hemoglobin reductase converts met-hemoglobin back to the native form of hemoglobin. Therefore, in the body, the toxic effects of the auto-oxidation of hemoglobin are prevented by specific enzyme-based reaction pathways that eliminate the unwanted by-products of oxygen metabolism.

The oxygen detoxification functions of superoxide dismutase, catalase, and glutathione peroxidase that protect red blood cells from oxygen toxicity during normal oxygen transport do not exist in the hemoglobin-based oxygen carriers (HBOC) developed to date. Without the oxygen detoxification function, the safety of the existing HBOC solutions will suffer due to the presence of toxic oxygen-related species.

The principle method by which the existing HBOC solutions are manufactured is through the removal of hemoglobin from the red cells and subsequent purification to remove all non-hemoglobin proteins and other impurities that may cause an adverse reaction during transfusion (See U.S. Pat. Nos. 4,780,210; 4,831,012; and 4,925,574). The substantial destruction or removal of the oxygen detoxification enzyme systems is an unavoidable result of the existing isolation and purification processes that yield the purified hemoglobin used in the HBOCs. Alternatively, instead of isolating and purifying hemoglobin from red cells, pure hemoglobin has been produced using recombinant techniques. However, recombinant human hemoglobin is also highly purified and does not contain the oxygen detoxification systems found in the red cells. Thus, the development of sophisticated techniques to create a highly purified hemoglobin solution is a mixed blessing because the purification processes remove the detrimental impurities and the beneficial oxygen detoxification enzymes normally present in the red cells ultimately leading to oxygen-related toxicity.

One of the observed toxic side effects of the existing HBOCs is vasoconstriction or hypertension. It is well known that the enzyme superoxide dismutase (SOD) in vitro will rapidly scavenge the superoxide anion and prolong the vasorelaxant effect of nitric oxide (NO). Nitric oxide is a molecule that has recently been discovered to be the substance previously known only as the "endothelium-derived relaxing factor" (EDRF). The prolongation of the vasorelaxant effect of nitric oxide by SOD has been ascribed to the ability of SOD to prevent the reaction between the superoxide anion and nitric oxide. (M. E. Murphy et. al., Proc. Natl. Acad. Sci. USA 88:10860 (1991); Ignarro et.al. J. Pharmacol. Exp. Ther. 244:81 (1988); Rubanyi Am. J. Physiol. 250: H822 (1986); Gryglewski et.al. Nature 320:454 (1986)).

However, in vivo, the inactivation of EDRF by the superoxide anion has not been observed and is not thought to be likely. Nevertheless, certain pathophysiological conditions that impair SOD activity could result in toxic effects caused by the superoxide anion (Ignarro L. J. Annu. Rev. Pharmacol. Toxicol. 30:535 (1990)). The hypertensive effect observed in preclinical animal studies of the existing HBOC solutions suggests that concentration of superoxide anion in large volume transfusions of the existing HBOCs is the cause for the destruction of EDRF and the observed vasoconstriction and systemic hypertension.

It is, therefore, important to delineate the hypertensive effect resulting from the reaction of the superoxide anion with nitric oxide (NO) from that resulting from extravasation and the binding of NO by hemoglobin. Upon transfusion of an HBOC, the hemoglobin can also depress the vasorelaxant action of nitric oxide by reacting with nitric oxide to yield the corresponding nitrosyl-heme (NO-heme) adduct. In particular, deoxy-hemoglobin is known to bind nitric oxide with an affinity which is several orders of magnitude higher than that of carbon monoxide. These hemoglobin-NO interactions have been used to assay for nitric oxide and to study the biological activity of nitric oxide. For example, the antagonism of the vasorelaxant effect of nitric oxide by hemoglobin appears to be dependent on the cell membrane permeability of hemoglobin. In intact platelets, hemoglobin did not reverse the effect of L-arginine which is the precursor of nitric oxide. In contrast, in the cytosol of lysed platelets, hemoglobin is the most effective inhibitor of L-arginine induced cyclic-GMP formation mediated by nitric oxide. These experiments demonstrated that the hemoglobin did not penetrate the platelet membrane effectively. (Radomski et.al. Br. J. Pharmacol. 101:325 (1990)). Therefore, one of the desired characteristics of the HBOCs is to eliminate the interaction of nitric oxide with hemoglobin. Hemoglobin is also known to antagonize both endothelium-dependent vascular relaxation (Martin W. et. al. J. Pharmacol. Exp. Ther. 232:708 (1985)) as well as NO-elicited vascular smooth muscle relaxation (Grueter C. A. et. al. J. Cyclic. Nucleotied Res. 5:211 (1979)). Attempts have been made to limit the extravasation and hypertensive effect of hemoglobin by chemically stabilizing, polymerizing, encapsulating, or conjugating the hemoglobin in the HBOCs to prolong the circulation time. Therefore, although the current HBOCs are relatively membrane impermeable and able to transport oxygen, the HBOC solutions do not have the capability of preventing the reaction between superoxide anion and nitric oxide when transfused.

An ideal solution to the toxicity problems of the existing blood substitutes would be a hemoglobin-based formulation that combines the oxygen-transport function of the existing HBOCs with the oxygen detoxification function of the red cells. However, a simple addition the enzyme superoxide dismutase into an existing HBOC solution would not be desirable because by reducing the concentration of superoxide anion, the reaction whereby hemoglobin is oxidized to met-hemoglobin would be encouraged, leading to an undesirable build-up of met-hemoglobin (See Equation [1]). Also, it is not desirable to encourage the conversion of the superoxide anion to hydrogen peroxide in a hemoglobin solution because the hydrogen peroxide is toxic and reactive and will decompose to toxic hydroxyl radicals or form other toxic organoperoxides during storage.

This invention contemplates the use of stable nitroxide free radicals, hereafter referred to as "nitroxide(s)", to provide the oxygen detoxification function of the red cells to hemoglobin-based blood substitutes. In the past, nitroxides have been used in electron spin resonance spectroscopy as "spin labels" for studying conformational and motional characteristics of biomacromolecules. Nitroxides have also been used to detect reactive free radical intermediates because their chemical structure provides a stable unpaired electron with well defined hyperfine interactions. In addition, nitroxides have been observed to act as enzyme mimics; certain low molecular weight nitroxides have been identified to mimic the activity of superoxide dismutase (SOD). (A. Samuni et. al. J. Biol. Chem. 263:17921 (1988)) and catalase (R. J. Mehlhorn et. al., Free Rad. Res. Comm., 17:157 (1992)). Numerous studies also show that nitroxides that are permeable to cell membranes are capable of short-term protection of mammalian cells against cytotoxicity from superoxide anion generated by hypoxanthine/xanthine oxidase and from hydrogen peroxide exposure.

A variety of techniques have been described to covalently attach a nitroxide to a biomacromolecules, including hemoglobin and liposomes. McConnell et. al., Quart. Rev. Biophys. 3:p.91 (1970); Hamilton et. al., "Structural Chemistry and Molecular Biology" A. Rich et. al., eds. W. H. Freeman, San Francisco, p.115 (1968); Griffith et. al., Acc. Chem. Res. 2:p.17 (1969); Smith I. C. P. "Biological Applications of Electron Spin Resonance Spectroscopy" Swartz, H. M. et. al., eds., Wiley/Interscience, New York p.483 (1972). Although selected nitroxides have been covalently bound to hemoglobin molecules for the purpose of studying cooperative oxygen binding mechanisms of hemoglobin, nitroxides have not been used in connection with hemoglobin that is specially formulated for use with blood substitutes. Experimental results are presented below to demonstrate that nitroxides may be attached to stabilized, polymerized, conjugated and encapsulated hemoglobin for use as a blood substitute.

SUMMARY OF THE INVENTION

This invention discloses compositions and methods using stable nitroxides in connection with hemoglobin-containing solutions. In particular, stable nitroxides are used with hemoglobin-containing solutions to create several formulations for a blood substitute that will possess the oxygen detoxification function of the red cells. These formulations are described herein as a hemoglobin-based red cell substitutes (HRCS) because the oxygen transport capability of the hemoglobin-based oxygen carriers (HBOC) is enhanced by providing the oxygen detoxification function of the body's red cells. In addition, this invention describes nitroxides that are covalently attached to the inner surface of a container or are attached to an insoluble matrix housed in a filter to be used with an existing HBOC to scavenge toxic oxygen-related compounds before infusion into a patient. The HRCS formulations described herein will alleviate the oxidative stress originating from the generation of the superoxide anion in the existing HBOC solutions, and upon transfusion, will diminish the destruction of nitric oxide, the endothelium-derived relaxing factor (EDRF). If the destruction of EDRF is prevented, the problem of vasoconstriction and systemic hypertension that are observed when the existing HBOC solutions are infused into a patient will be substantially alleviated.

The HRCS formulations described below retard the formation of toxic oxygen-related species by causing a nitroxide to function as a "superoxide oxidase," an enzyme-like reaction not known to occur in the red cells. In these HRCS formulations, the nitroxide prevents the accumulation of the undesirable superoxide anion generated from the autooxidation of hemoglobin (See Equation [1]). In the "superoxide oxidase" reaction, the superoxide anion is oxidized back into molecular oxygen without proceeding to the formation of hydrogen peroxide. This is accomplished in part by creating a storage condition wherein the concentration of nitroxide greatly exceeds that of oxygen. Used in the manner disclosed herein, the nitroxide prevents the cascade of undesirable oxidative reactions that begin with the formation of the superoxide anion. Furthermore, the physiologically compatible HRCS solutions described here will offer advantages over the existing HBOC solutions because the nitroxide will mimic the enzymatic activity of superoxide dismutase and catalase after the formulations described herein are infused into a patient.

Preferred compositions using nitroxide in connection with a physiologically compatible hemoglobin solutions include: 1) nitroxide attached to a storage container or covalently attached to an insoluble matrix used as a filter, 2) nitroxide covalently linked to hemoglobin that is stabilized by chemical or recombinant cross-linking, 3) nitroxide covalently linked to polymerized hemoglobin, 4) nitroxide co-encapsulated with hemoglobin inside a liposome or intercalated into a liposome membrane, and (5) nitroxide covalently bound to conjugated hemoglobin.

Also, HRCS based on the co-encapsulation of a membrane-impermeable nitroxide with hemoglobin is disclosed. Finally, the methods of preparing the above formulations are described as are methods for producing nitroxide-containing filters and containers for the storage and detoxification of an existing HBOC.

DESCRIPTION OF DRAWINGS

FIGS. 4A and 4B, respectively, are electron spin resonance spectra demonstrating 4-amino-TEMPO labelled and o-raffinose cross-linked and polymerized human hemoglobin and 3-maleimido-PROXYL labelled DBBF-hemoglobin polymerized with glutaldehyde.

DETAILED DESCRIPTION OF THE INVENTION

Figure 1A:
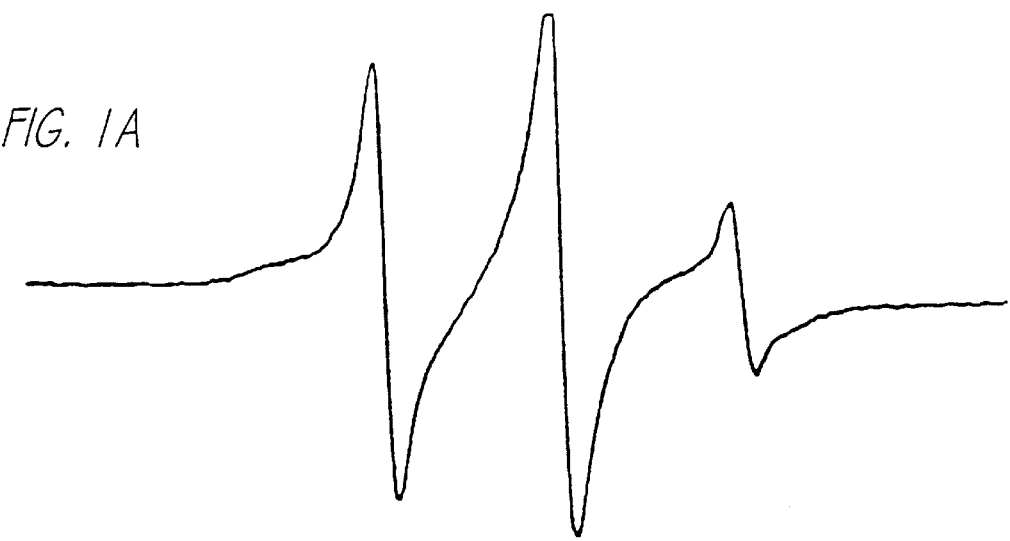
FIGS. 1A and 1B show the electron spin resonance spectra of 4-amino-TEMPO labelled o-raffinose polymerized hemoglobin recorded on (A) day 1 and (B) day 30.

The term "hemoglobin" is used generally herein to describe oxy-, carboxy-, carbonmonoxy-, and deoxy-hemoglobin except as otherwise noted by the context of the description. The hemoglobin used with this invention may be human, recombinant or animal in origin and is obtained and purified by known techniques. The hemoglobin may be covalently bound to pyridoxal groups of pyridoxal-5'-phosphate or ring opened adenosine triphosphate (o-ATP) by reaction with the aldehyde groups and cross-linked derivatives of hemoglobin. The cross-linked derivatives may include polyfunctional, heterobifunctional and homobifunctional cross-linking regents such as dialdehyde, polyaldehyde, diepoxide, polyepoxide, activated polycarboxyl and dicarboxyl groups, for example, 3,5-bisbromosilicyl-bisfumarate, and TEMPO succinate or TOPS See (U.S. Pat. No. 4,240,797) cyclodextrans and their anionic (e.g., sulfate) cross-linked hemoglobin as well as polymerized hemoglobin. All hemoglobin solutions described herein for use with this invention are physiologically compatible. The hemoglobin solutions are cell-free to remove pyrogens, endotoxins, and other contaminants.

The term "nitroxide" is used herein to describe stable nitroxide free radicals, their precursors, and their derivatives thereof including the corresponding hydroxylamine derivative where the oxygen atoms are replaced with a hydroxyl group and exist in hydrogen halide form. For the purposes of this invention, the chloride salt form of the hydroxylamine derivatives are preferred.

In the nitroxides described here, the unpaired electron of a nitroxide is stable in part because the nitrogen nucleus is attached to two carbon atoms which are substituted with strong electron donors. With the partial negative charge on the oxygen of the N—O bond, the two adjacent carbon atoms together localize the unpaired electron on the nitrogen nucleus.

Nitroxides may have either a heterocyclic or linear structure. The fundamental criterion is a stable free radical. Structurally, nitroxides of the following formula are preferred where $R_1$–$R_4$ are electron donors and A is the remaining members of a heterocyclic ring.

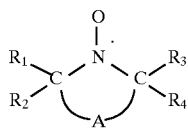

In these heterocyclic structures, "A" represents the remaining carbon atoms of a 5-membered (pyrrolidinyl or PROXYL with one double bond, i.e., pyrroline) or a 6-membered (piperidinyl or TEMPO) heterocyclic structure and in which one carbon atoms may be substituted with an oxygen atom (oxazolinyl or DOXYL) and certain hydrogen atoms may be substituted with up to two bromine atoms. In such heterocyclic structures, stable isotopes may be utilized (e.g., $N_{15}$, deuterium). Substitution at the α carbons should be such that the unpaired electron is maintained substantially in a πp orbital configuration. $R_1$ through $R_4$ are alkyls (straight and branched chain) or aryl groups but are preferred to be methyl or ethyl groups. The substituent groups on the alpha carbons in any nitroxide should be strong electron donors to enhance stability, thus methyl ($CH_3$) groups or ethyl ($C_2H_5$) groups are preferred although other longer carbon chain species could be used. In practice, steric considerations may limit the scope of the nitroxide compounds that are practical and economical. The preferred nitroxides used with this invention include nitroxides having the following structure

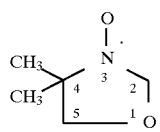 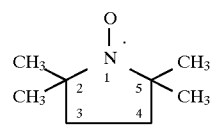

DOXYL
(4,4-Dimethyl-3-oxazolinyloxy-)
(4,4-Dimethyloxazolidine-N-oxyl)

PROXYL
(2,2,5,5-Tetramethyl-1-pyrrolidinyloxy-)
(2,2,5,5-Tetramethypyrrolidine-N-oxyl)

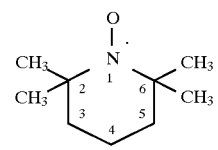

TEMPO
(2,2,6,6--Tetramethyl-1-piperidinyloxy-)
(2,26,6-Tetramethylpiperidine-N-oxyl)

As is apparent from the above, most suitable nitroxide compounds may be represented basically by the structural formula

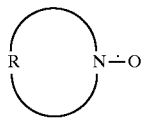

assuming that the R group is selected from among the configurations which preserve the stability of the free radical.

The nitroxides which can be employed in this invention are structurally diverse because the requisite property of the nitroxides is their ability to influence the course of the superoxide anion cascade in HRCS by mimicking the superoxide oxidase, superoxide dismutase, and catalase activities without substantially being consumed in the process. Although a wide variety of nitroxides may be used with this invention, the nitroxide should be physiologically acceptable at a minimum concentration required to alleviate oxygen toxicity in the HRCS. In assessing an operative species, it is noteworthy that the relatively low toxicity of nitroxides has encouraged their development as contrasting agent in NMR imaging (See U.S. Pat. Nos. 4,834,964; 4,863,717; 5,104,641).

A number of methods for isolating and purifying hemoglobin solutions such that they are physiologically compatible are known to those skilled in the art. Typically, purified hemoglobin compositions contain at least 99% hemoglobin by weight of total protein, a total phospholipid content of less than about 3 ug/ml, less than 1 ug/ml of either phosphatidylserine or phosphatidylethanolamine and an inactive heme pigment of less than 6%. The purified hemoglobin solutions which are useful in this invention can be prepared using a variety of conventional techniques, including but are not limited to, those disclosed in Cheung et. al., Anal Biochem 137:481–484 (1984), De Venuto et. al., J. Lab. Clin. fled. 89:509–516 (1977), and Lee, et. al., VIth International Symposium on Blood Substitutes, San Diego, Calif. Mar. 17–20 Abstract H51 (1993).

The purified hemoglobin solutions used in this invention should be essentially free of oxygen. Hemoglobin in solution may be deoxygenated by admixture with a chemical reducing agent which causes the hemoglobin to release oxygen and to be maintained in a substantially deoxygenated state. A preferred method for deoxygenating a hemoglobin solution is performed by exposing a hemoglobin solution to an inert, essentially oxygen-free gas, such as nitrogen or carbon monoxide to cause removal of bound oxygen from the hemoglobin and conversion of the hemoglobin in solution to a form such as deoxy-hemoglobin or carbonmonoxy-hemoglobin that lacks oxygen. Alternatively, hemoglobin may be exposed to a vacuum or gas through a membrane that is permeable to oxygen yet impermeable to hemoglobin. For example, a hemoglobin solution may be passed through a diffusion cell having a membrane wall along which hemoglobin flows and through which oxygen is capable of passing, but hemoglobin is not. Inert gas is circulated along the side of the membrane wall opposite the hemoglobin solution causing the removal of oxygen and the conversion of the hemoglobin in solution to the deoxygenated state. Preferably, the deoxy-hemoglobin is maintained in an essentially oxygen-free environment during nitroxide labelling, cross-linking, polymerization, or conjugation.

After removal of any bound oxygen, a nitroxide is covalently attached to the hemoglobin. Normally at least one, and preferably more than one, nitroxide will be covalently attached to a single hemoglobin molecule. The nitroxide may be covalently attached to the hemoglobin at any of several sites on the hemoglobin molecule including:

(a) at one or more of the free sulfhydro (—SH) groups, for example, at the β-93 site;

(b) at any reactive amino (—NH$_2$) groups, for example, in the DPG site at Val-1 of the β-chain and/or lysine-82 of the β-chain and/or lysine-99 of the α-chain;

(c) at any non-specific surface amino (—NH$_2$) or carboxyl (—COOH) group;

A nitroxide may also be bound to any residual aldehyde, epoxy, or activated carboxyl groups of a divalent- or a multivalent-cross-linker involved in the cross-linking and polymerization of hemoglobin or at any residual reactive groups on an agent such as dextran (Dx) or hydroxylethyl-starch (HES) or polyoxyethylene (POE) used to conjugate hemoglobin.

As described in Equation [1], above, during the storage period, the hemoglobin in an HBOC solution is slowly auto-oxidized by oxygen to form met-hemoglobin and the superoxide anion. However, during the storage of the HRCS that are the subject of this invention, the superoxide anion thus formed will reduce the nitroxide to a hydroxylamine derivative, and the superoxide anion will be oxidized to form molecular oxygen by the following reaction.

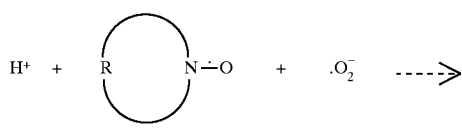

[4]

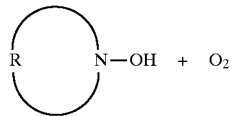

The conversion of superoxide anion to molecular oxygen described in Equation [4] prevents the accumulation of superoxide anion and the subsequent formation of hydrogen peroxide. This activity, described herein as a "superoxide oxidase" activity, will be most effective when the initial oxygen content in the composition is kept to a minimum, the composition is stored in an essentially oxygen free environment and the nitroxide concentration is sufficient to prevent the formation of superoxide anion and hydrogen peroxide. Therefore, storage of the HRCS in an essentially oxygen-free container is preferred.

Container systems that permit a solution to be stored in an oxygen free environment are well known because many non-hemoglobin based intravenous solutions are sensitive to oxygen. For example, a glass container that is purged of oxygen during the filling and sealing process may be used. Also, flexible plastic containers are available that may be enclosed in an overwrap to seal against oxygen. Basically, any container that prevents oxygen from interacting with hemoglobin in solution may be used.

Figure 1B:
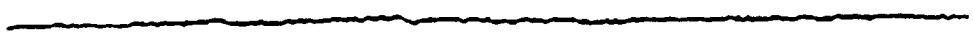

To demonstrate the "superoxide oxidase" activity of a nitroxide, samples of nitroxide-labelled hemoglobin in solution are kept in an accelerated oxidative storage condition and the redox state of the nitroxide is studied over time by electron spin resonance spectroscopy. For example, an o-raffinose polymerized hemoglobin solution that has been labelled with 4-amino-TEMPO is stored in its oxygenated state in a sealed glass container (FIG. 1A). In such a state, the rate of superoxide anion and met-hemoglobin formation in solution is sufficiently rapid that the conversion of the nitroxide to its hydroxylamine derivatives may be conveniently monitored (See Equation [4] and compare FIGS. 1A and 1B). Equation 4 represents that the conversion of nitroxide to its diamagnetic hydroxyl derivative is coupled to the conversion of the superoxide anion back to molecular oxygen. The experimental evidence in support of such a conversion is shown in FIGS. 1A and 1B. The electron spin resonance spectrum of TEMPO covalently attached to the hemoglobin (FIG. 1A) was converted to its diamagnetic derivatives which result in the complete disappearance of the resonance peaks after storage of the sample for 30 days at 4° C. (FIG. 1B). The nitroxide is considered to have performed a "superoxide oxidase"-like activity when it is converted to its hydroxylamine derivative in the presence of hemoglobin.

Figure 1C:
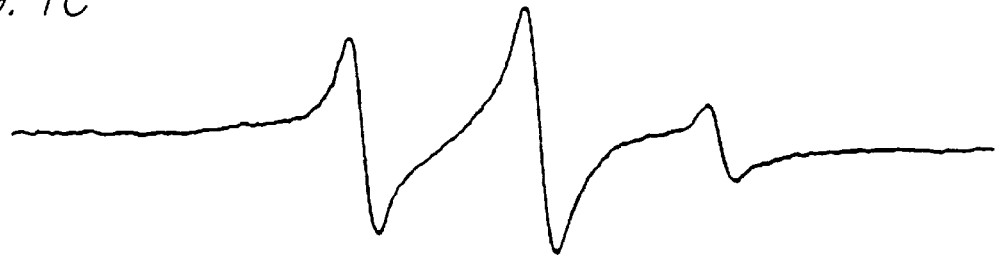
FIG. 1C is the spectra of the sample in FIG. 1A diluted with equal volume of unlabelled hemoglobin recorded on day 1.
Figure 1D:
FIG. 1D is the sample in FIG. 1C recorded on day 30.

The "superoxide dismutase" activity of a nitroxide in an HBOC solution is demonstrated by showing the reconversion of the hydroxylamine derivative back to a nitroxide (See Equation [5] together with Equation [4]). Knowing that under the experimental conditions described in FIGS. 1A and 1B the nitroxide is fully converted to hydroxylamine (See Equation [4]), the nitroxide may be regenerated by simply providing more superoxide anion as shown in Equation 5. To demonstrate this reaction mechanism, the relative concentration of hemoglobin (and thus superoxide anion) to the nitroxide is increased by diluting the sample in FIG. 1A with an equal volume of unlabelled hemoglobin. A comparison of FIGS. 1A and 1C shows an approximate 50% reduction of the signal intensity of the nitroxide due to the dilution effect. On the other hand, after 30 days of cold storage at 4° C., the nitroxide was partially regenerated (See FIG. 1D) as predicted by Equation [5]. This observation is consistent with the reconversion of the hydroxylamine derivative to nitroxide coupled with the formation of hydrogen peroxide from superoxide anion.

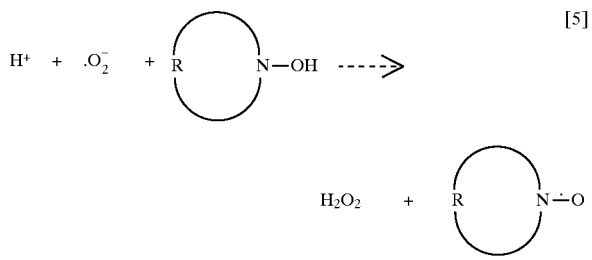

Summing equations [4] and [5] results in:

$$2 \cdot O_2^- + 2H^+ \rightarrow O_2 + H_2O_2$$

which demonstrate that the nitroxide acts as a low molecular weight, metal-free, SOD mimic in "HBOC" solutions. The detection of electron spin resonance spectrum of the nitroxide (in FIG. 1D) is consistent with the reaction of superoxide anion with the hydroxylamine

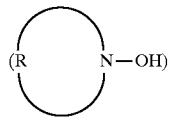

resulting in the formation of nitroxide

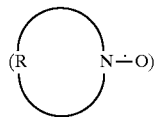

and hydrogen peroxide ($H_2O_2$).

The number of nitroxide molecules per hemoglobin molecule may be in the range of approximately 1–20 and is most preferably at about 2. However, the nitroxide-hemoglobin ratio should be kept to a minimum due to pharmacokinetic, toxicological and immunological considerations. For example, a nitroxide such as 3-maleimido-PROXYL is covalently bound to hemoglobin in solution by first preparing a 100 mM solution of the nitroxide in ethanol as the carrier solvent. Two(2) molar equivalents of the nitroxide to hemoglobin was added directly with mixing to a DCL-Hb (8 g/dl)in Lactated Ringers. The reaction mixture was allowed to react at 22° C. with agitation until greater than 90% of the nitroxide was covalently linked to the DCL-Hb, usually within one hour. The unreacted nitroxide was then removed with a cross-flow membrane filtration system having a molecular-weight cutoff of 30,000 daltons by washing three (3) times with 10 volumes of Lactated Ringers. The retantate hemoglobin concentration is adjusted to between 7–14 g/dl, sterile filtered, and stored at 4° C. After transfusion, when the HRCS is fully oxygenated, the nitroxide is expected to function as a SOD-mimic and secondly as a catalase-mimic. As an SOD-mimic it dismutates the superoxide anion to hydrogen peroxide (See Equation [2]) and consequently protect against the destruction of nitric oxide in the endothelium to prevent vasoconstriction. As a catalase-mimic it prevents hydrogen peroxide toxicity by converting the latter to harmless water (See Equation [3]).

As noted above, nitroxides have been covalently bound to hemoglobin to study the cooperative oxygen binding properties of the hemoglobin molecule itself. However, nitroxides have not been used with stabilized, i.e., cross-linked, or polymerized, encapsulated, or conjugated hemoglobin solution that are physiologically compatible. The known chemistry of hemoglobin and nitroxides suggests that it is possible to perform similar nitroxide-labelling of hemoglobin that has been chemically cross-linked or cross-linked through recombinant techniques by selecting an available site on the hemoglobin molecule that is not blocked by the particular compound used to stabilize, polymerize, or conjugate the hemoglobin molecule(s). Because certain of the stabilized and polymerized forms of hemoglobin described below are currently involved in clinical trials, the attachment of nitroxides to these stabilized and polymerized hemoglobin-based oxygen carriers is described below in the context of the first, second, and third preferred embodiments to demonstrate that the oxygen detoxification function of this invention is applicable to the existing hemoglobin solutions.

I. First Preferred Embodiment—Nitroxide Labelled Containers and Filters for HBOC Is it possible to provide the oxygen-detoxification function of this invention to existing HBOC solutions without chemically modifying the hemoglobin in these formulations. By covalently attaching nitroxides to a surface inside the vessel in which the HBOC is stored, this invention may alleviate the adverse physiological effects caused by oxygen toxicity that are observed with the existing formulations.

The container used with the hemoglobin-containing solutions that are the subject of this invention should be physiologically compatible having similar characteristics as any container to be used with intravenous fluids. Typically, glass or a biocompatible plastic is suitable. For the embodiments of the invention where a solution containing hemoglobin is placed in a container for any length of time, the container should be oxygen free and capable of being sealed to exclude oxygen. With a glass container, a traditional stopper and closure means is sufficient. However, some of the flexible plastic containers currently available are oxygen permeable. In this case, a foil overwrap or other sealing mechanism may be used to prevent oxygen from contacting the hemoglobin in solution.

To apply a nitroxide to an inner surface of a container, a non-leaching layer of a nitroxide polymer or a nitroxide-doped copolymer is coated directly on the inner surface. Nitroxide-containing polymers can be created by a number of techniques based on generally known principles of polymerization as long as the stability of the free radical is maintained in the polymerization process.

Also, the interior surface of an HBOC container may be modified to contain a coating layer of a substance that can bind a nitroxide, such as hydrophilic hydrazide groups which will react with the ketone or the aldehyde group of a nitroxide to form stable hydrazone derivatives. The coating reaction is straight forward. For example, the nitroxide (100 mM) in acetate buffer at pH 5.0 is added to a hydrazide activated plastic container to facilitate the formation of a hydrazone linkage.

Once the container is prepared, a physiologically compatible solution is added. This solution may be a stabilized and purified HBOC or the HRCS disclosed herein, but could also include any intravenous colloid or crystalloid solution that is desirable to co-infuse with hemoglobin. The solution is then maintained in an essentially oxygen-free environment.

In addition to treating a surface inside a container, a filter-type cartridge, with a luer lock inlet and outlet, containing a gel or solid matrix upon which a nitroxide is immobilized may be used to remove reactive oxygen-derived reactive species while the hemoglobin solution passes through the cartridge. In these applications, the nitroxide is bound to a soft- or hard-gel matrix through which the HBOC passes, functioning essentially as a sterile in-line filter, prior to infusion. A variety of methods to attach small ligands, such as nitroxide, to a solid matrix are well known in the art of affinity chromatography, as are the techniques to chemically modify glass and plastic surfaces. Several types of matrices that are compatible with sterile solutions are known including agarose gel, polysulfone-based material, latex, and others.

Figure 7:
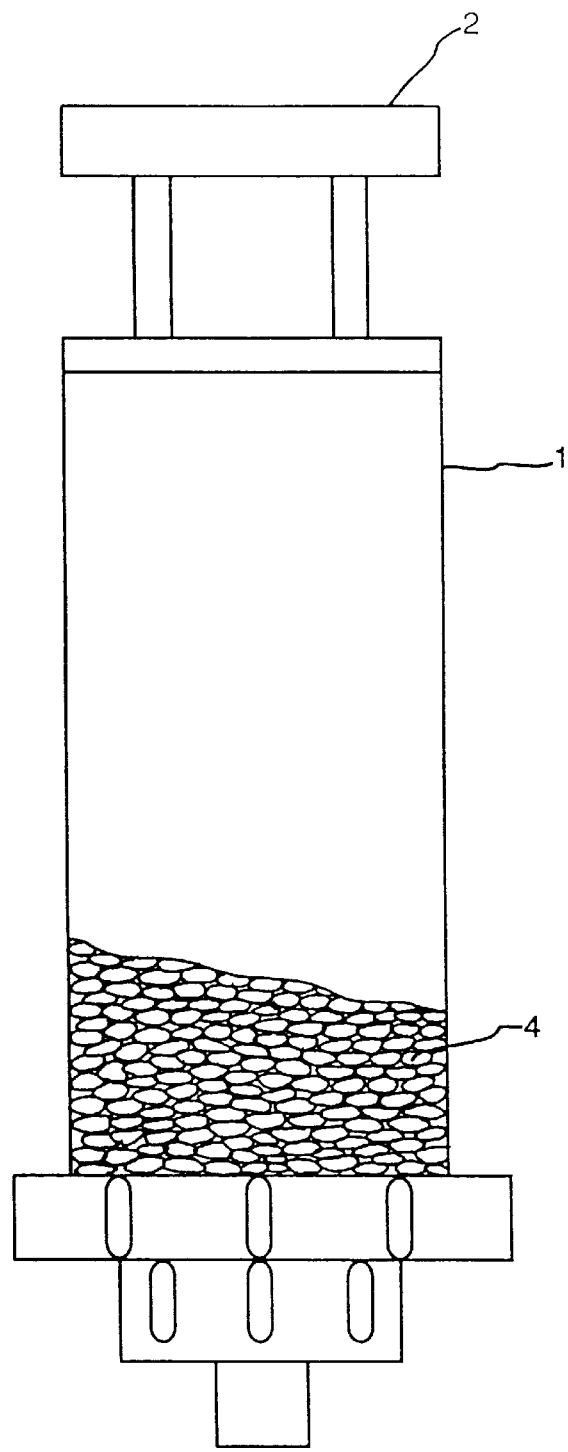
FIG. 7 is an embodiment of a filter cartridge that contains a solid matrix to which a nitroxide is bound and through which a hemoglobin-containing solution may be passed.

In the filter cartridge approach, the solid matrix is covalently linked with a nitroxide and contained in a filter housing or other such apparatus such that a hemoglobin solution can flow through the apparatus and be brought into contact with a nitroxide while being infused into a patient. A practical approach is to use a commonly available activated agarose gel as the matrix and contain the gel in a sterile luer lock cartridge. The cartridge is then simply inserted in the fluid administration line during the transfusion of a solution containing hemoglobin. In practice, the structure that comprises the filter housing in which the nitroxide and through which hemoglobin is passed can be provided by a variety of known structures. Referring now to FIG. 7, housing 1 contains a nitroxide-labelled agarose gel. For example, a 4-bromoacetamido-TEMPO labelled ω-aminohexylagarose (See FIG. 2A) a 1,4-bis(2,3-epoxypropoxy)butane agarose coupled with 4-amino-TEMPO (See FIG. 2B).

Figure 2A:
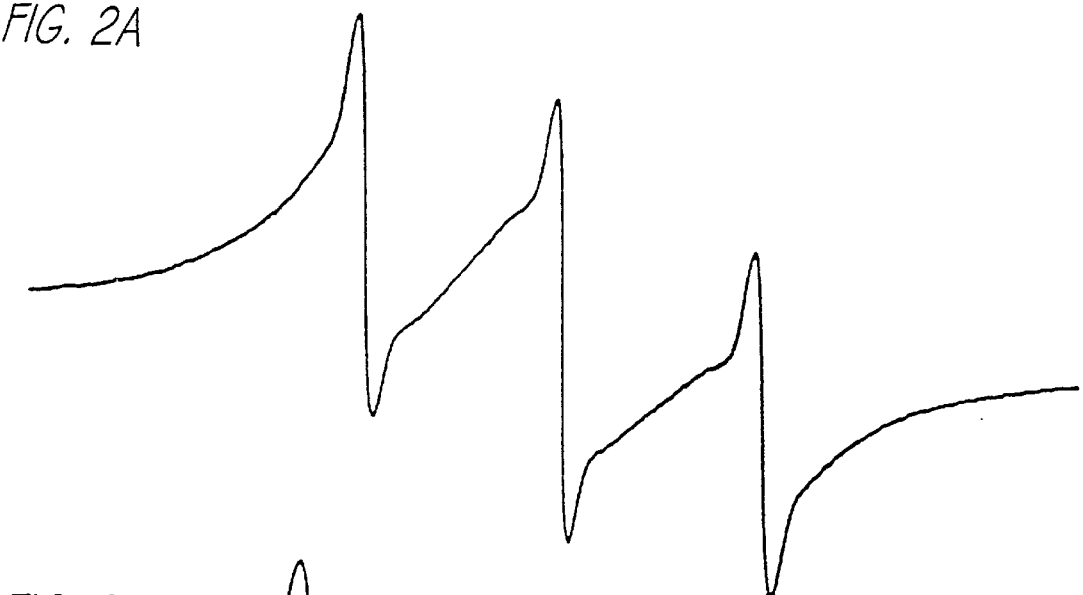
FIGS. 2 and 2B are, respectively, the electron spin resonance spectra demonstrating covalent attachment of 4-(2-bromoacetamido)-TEMPO to ω-aminohexyl-agarose and 4-amino-TEMPO to 1,4-bis(2:3-Epoxypropoxy) butane-activated agarose.
Figure 2B:
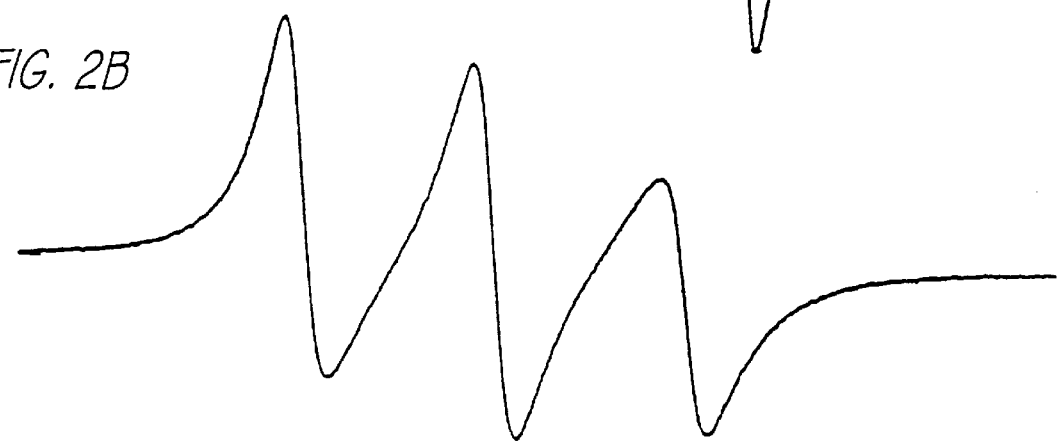

During the transfusion, the intravenous transfusion line containing a hemoglobin solution would be connected to the luer inlet 2 allowed to enter the housing 1 wherein the hemoglobin solution would encounter the nitroxide bound to the matrix 4 to remove the toxic oxygen-related species. The hemoglobin solution would then pass out of the cartridge through the luer outlet 3 and would be directly transfused into a patient. The electron resonance spectrum of 4-amino-TEMPO labelled epoxy-agarose is shown in FIG. 2A. Alternatively, an ω-aminohexyl-agarose may be reacted with 4-(2-bromoacetamido)-TEMPO to form TEMPO labelled agarose. The electron spin resonance spectrum is shown in FIG. 2B. An alternative would be to couple the 4-carboxyl-TEMPO to the amino-agarose with carbodiimide via a carboamide linkage. Conversely, the 4-amino-TEMPO is readily coupled to the carboxyl group on an agarose gel using carbodiimide, for example, 1-ethyl-3-(3-dimethylamino-propyl)carbodiimide.

The cartridge labelled with 4-amino-TEMPO prepared by circulating a 100 mM 4-amino-TEMPO (Sigma Chem. Co.) in a Lactated Ringers solution through an aldehyde Avid-Chrom Cartridge (Unisyn Tech. Inc.) at room temperature for one hour followed by the reduction with sodium cyanoborohydride for six(6) hours. The interior of the cartridge housing is thoroughly washed with Lactated Ringers.

The cartridge labelled with 3-amino-PROXYL may be similarly prepared by substituting 4-amino-TEMPO with 3-amino-PROXYL according to the procedure described above.

II. Second Preferred Embodiment—Nitroxide-Labelled Stabilized Hemoglobin

To prevent dissociation of hemoglobin into its constituent subunits, hemoglobin is intramolecularly stabilized by chemical or recombinant cross-linking of its subunits. "Stabilized" hemoglobin is referred herein to describe hemoglobin monomers that are stabilized by chemical or recombinant cross-linking and also to describe dimers, trimers, and larger oligomers whose constituent hemoglobin molecules are stabilized by cross-linking with cyclodextrans and their sulfated derivatives.

A preferred technique for attaching nitroxide to stabilized hemoglobin is by the covalent attachment of the nitroxide to the β-93 sulfhydryl groups of the two β-chains of stabilized hemoglobin. Although specific labelling at the β-93 site has been demonstrated on native human hemoglobin for conformational studies (See review by McConnell et. al., Quart. Rev. Biophys. 3:91 (1970)), such a specific labelling of cross-linked hemoglobin has not been reported. As noted above, several types of hemoglobin-based oxygen carriers have been developed that are stabilized through chemical cross-linking with DBBF, diaspirin cross-linked hemoglobin and hemoglobin that is stabilized and oligomerized with o-raffinose.

The ring opened sugars described in my U.S. Pat. No. 4,857,636 yield polyvalent aldehydes derived from disaccharides, oligosaccharides, or, preferably, trisaccharides such as o-raffinose. These compounds function both to provide intramolecular stabilization (cross-linking) and intermolecular polymerization. By controlling the reaction disclosed in my earlier patent, the polyvalent aldehydes may be used to produce "stabilized" hemoglobin as defined above without polymerization. In another case, a nitroxide may be covalently bound to the stabilized hemoglobin or the polymerized hemoglobin. Therefore, the hemoglobin-based solutions that are stabilized using the polyvalent aldehydes are considered in the present embodiment as a "stabilized" hemoglobin and in the subsequent embodiment as a polymerized hemoglobin.

To demonstrate, that the β-93 site of the chemically modified hemoglobin has not been rendered sterically inaccessible for nitroxide attachment, results are presented to confirm that a nitroxide may be covalently bound to the β-93 site of DBBF-Hb.

In this embodiment, DBBF-Hb is reacted with two types of nitroxides (TEMPO and PROXYL) which contain two types of sulfhydro group specific functional groups and have the following structural formula:

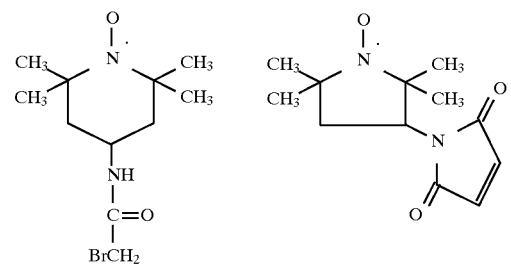

4-(2-Bromoacetamido)-TEMPO  3-Maleimido-PROXYL

Figure 3A:
FIGS. 3A and 3B, respectively, are electron spin resonance spectra demonstrating successful covalent attachment of 4-(2-Bromoacetamido)-TEMPO and 3-maleimido-PROXYL to 3,5-bis-bromosilicyl-bisfumarate (DBBF) cross-linked or diaspirin cross-linked human hemoglobin.
Figure 3B:
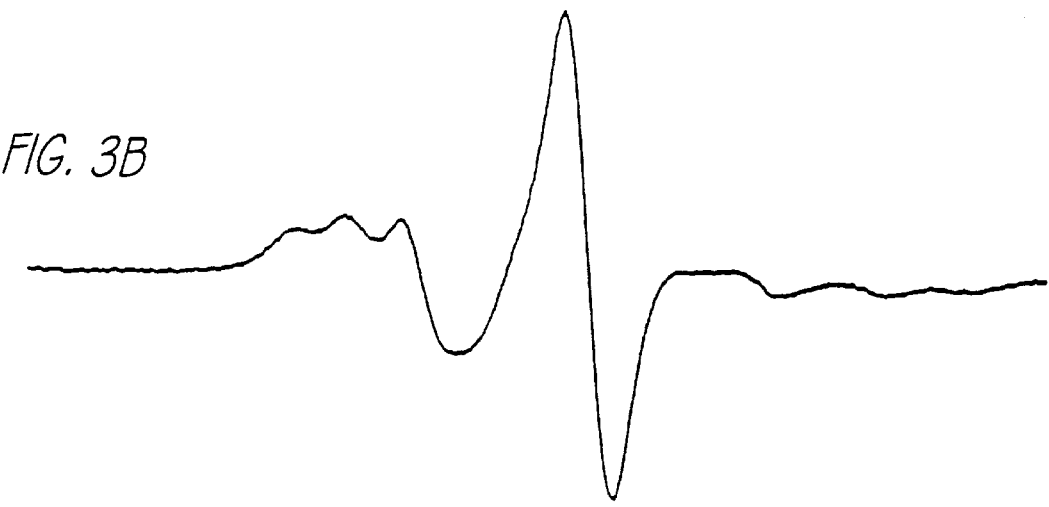

DBBF-Hb is prepared by cross-linking purified deoxygenated hemoglobin in solution with bis(3,5 dibromosalicyl) fumarate rate by known techniques, and the resulting product is purified by column chromatography. The covalent attachment of 3-maleimido (2,2,5,5-tetramethyl pyrrolidine-N-Oxyl) [3-maleimido-PROXYL] is accomplished by adding 2 molar equivalents of this nitroxide using methanol as the carrier solvent at a concentration of approximately 100 mM of 3-maleimido-PROXYL to 1 ml of DBBF-Hb at a concentration of approximately 8 g/dl in Lactate Ringers. The DBBF-Hb is allowed to react at 22–23½ C. for approximately 30 minutes with mixing. The extent of cross-linking is estimated from the percent disappearance of the electron spin resonance signal intensity of the unreacted nitroxide. To remove the unreacted nitroxide, the reaction mixture was washed three (3) times with a 10 volume excess of Lactated Ringers using a Filtron stire cell with a 30 kilodalton cut-off nominal molecular weight limits (NMWL) polyethylene sulfone (PES) membrane (Filtron Technology Co.). The electron spin resonance measurements of the nitroxide labeled hemoglobin was recorded with a Bruker ESR spectrometer. FIG. 3A shows the electron spin resonance spectra of 3-maleimido-PROXYL labelled DBBF-Hb. The electron spin resonance spectrum of DBBF-Hb that is similarly labelled with 4-(2-bromoacetamido)-TEMPO is shown in FIG. 3B.

In this embodiment, the nitroxide is covalently linked to the lone sulfhydro group on the two β-globin chains of hemoglobin. Thus, the nitroxide to hemoglobin-bound oxygen ratio is approximately 200 to 1 at 99.00% deoxyhemoglobin because there are two nitroxides attached to the two β-globin chains of the hemoglobin. After transfusion, however, the deoxygenated HRCS picks up oxygen in the lung and the nitroxide to hemoglobin-bound oxygen ratio becomes approximately 1 to 2 at 100% oxygenation because there are four oxygen molecules bound to the four globin chains of the hemoglobin with the two nitroxides remaining on the β-globin chains.

Using a hemoglobin-to-nitroxide ratio of 1:2, greater than 90% of the nitroxide is covalently attached to the DBBF-Hb. DBBF-Hb may also be covalently labelled with a spacer group (e.g., an extra methyl group) between the maleimido and PROXYL moieties (i.e., 3-maleimidomethyl-PROXYL) which would exhibit a resonance spectrum similar to that of FIG. 3B. It is noteworthy that other nitroxides may be covalently attached to specific amino-groups in the DPG binding site (e.g., β-Val-1 β-Lys-82 and α-Lys-99) or may be attached to the remaining 40-plus surface lysine ε-amino groups on hemoglobin. Isothiocyanate derivatives of the TEMPO and PROXYL nitroxides are also reactive with the amino group. For example, 4-isothiocyanate-TEMPO may be added to hemoglobin at a molar ratio of approximately 10:1. Resonance spectrum (not shown) of hemoglobin labelled with this nitroxide at other sites is similar to that shown in FIG. 3A.

The ability to attach nitroxides at several sites of DBBF-Hb suggests that recombinant hemoglobin that is stabilized with alpha-globin dimers (D. Looker et.al. NATURE 356:258 (1992)) may be similarly labelled with a nitroxide. It is also possible to prepare a DBBF analogue of a nitroxide labelled cross-linking agent such as a TEMPO labelled succinate (See U.S. Pat. No. 4,240,797).

III. Third Preferred Embodiment—Nitroxide-Labelled Polymers of Stabilized Hemoglobin While it is possible to produce dimers of stabilized hemoglobin from cross-linked monomers, it is also possible to produce hemoglobin polymers from stabilized or native hemoglobin. Solutions of hemoglobin polymers contain a mixture of monomers, dimers, trimers, tetramers, and other oligomers. Solutions containing polymerized hemoglobins used as an HBOC generally have longer plasma circulation times and higher oxygen carrying capacities as compared to stabilized monomeric hemoglobin. Such polymerized hemoglobin may be prepared by a number of pathways using several different polymerizing agents. (See, U.S. Pat. Nos. 4,001,200, 4,857,636, and 4,826,811). The preferred method of introducing a nitroxide to a solution of polymerized hemoglobin is again by covalently attaching a nitroxide to the β-93 sulfhydryl groups of the two β-globin chains of hemoglobin. These sulfhydryl groups are not known to be involved in the stabilization or polymerization processes. Consequently, the nitroxide is preferably covalently attached to hemoglobin before the stabilization and polymerization of the hemoglobin monomers.

For example, nitroxide is covalently attached to DBBF-Hb according to the procedure described in the second embodiment above, followed by polymerization with glutaldehyde according to the procedure described in Sehgal et. al. U.S. Pat. No. 4,826,811. FIG. 4B is an electron spin resonance spectra of the DBBF-Hb labelled with 3-maleimido-PROXYL and polymerized with glutaldehyde. Similarly, DBBF-Hb that is polymerized with glutaldehyde may be labelled with 4-(2-bromoacetamido)-TEMPO by the same method.

Using a similar approach, a polymerized hemoglobin intermediate, such as a glutaldehyde-polymerized or an o-raffinose-polymerized hemoglobin intermediate that contains unreacted aldehyde groups, may be used for covalent attachment of either 4-amino-TEMPO or 3-amino-PROXYL via reductive amination to yield a nitroxide-labelled hemoglobin polymer. With reductive amination, the sequence and timing of the reaction are important. The 4-amino-TEMPO is added to glutaldehyde-polymerized hemoglobin after completion of polymerization, but prior to the reduction reaction that results in covalent attachment of the nitroxide to the polymerized hemoglobin. Likewise, the nitroxide labelling of a o-raffinose polymerized hemoglobin may be accomplished by the addition of either 4-amino-TEMPO or 3-amino-PROXYL prior to reductive amination. For example, 4-amino-TEMPO labelled o-raffinose polymerized hemoglobin is prepared according to the procedure described in my U.S. Pat. No. 4,857,636 except that 6 molar equivalents of 4-amino-TEMPO is added after the completion of the polymerization and prior to the reduction with 20 molar excess of borane dimethylamine complex. As described therein, hemoglobin may be cross-linked and polymerized using polyvalent aldehydes derived from disaccharides or ring-opened sugars including, oligosaccharides, or preferably, trisaccharides such as o-raffinose. Likewise, monosaccharides may be used to stabilize and polymerize hemoglobin although the higher molecular weight sugars are preferred. The resonance spectrum of a dialyzed and washed o-raffinose polymerized hemoglobin labelled with 4-amino-TEMPO was shown in FIG. 4A.

IV. Fourth Preferred Embodiment—Nitroxide-Labelled Liposome-Encapsulated Hemoglobin Liposomes are particles which are formed from the aggregation of amphophilic molecules to form a bilayer structure in a hollow spherical shape with the polar sides facing an internal water compartment and external bulk water. Several acceptable methods for forming liposomes are known in the art. Typically, molecules form liposomes in aqueous solution like dipalmitoyl phosphatidylcholine. Liposomes may be formulated with cholesterol for added stability and may include other materials such as neutral lipids, and surface modifiers such as positively or negatively charged compounds. The preferred liposomes are small unilamellar-bilayered spherical shells.

A method for encapsulating hemoglobin in a liposome is also known (See Farmer et. al., U.S. Pat. No. 4,911,921). For the purpose of this invention, a number of approaches may be used to introduce the nitroxide-based oxygen detoxification function to a solution of liposome-encapsulated hemoglobin. For example, it is possible to use nitroxide-labelled native hemoglobin, or a nitroxide-labelled stabilized hemoglobin as disclosed above, as the starting material and then performing the process of liposome encapsulation of the nitroxide-labelled hemoglobin by known techniques. In the present embodiment, purified hemoglobin may also be coencapsulated with a membrane impermeable nitroxide such as TEMPO-choline chloride disclosed for a spin membrane immunoassay in Hsia et. al. U.S. Pat. No. 4,235,792.

Figure 5A:
FIGS. 5A, 5B, and 5C, respectively, are electron spin resonance spectra of liposome encapsulated human hemoglobin containing (A) 3-DOXYL-cholestane (B) 16-DOXYL-stearic acid and (C) both 3-DOXYL-cholestane and 16-DOXYL-stearate.
Figure 5B:
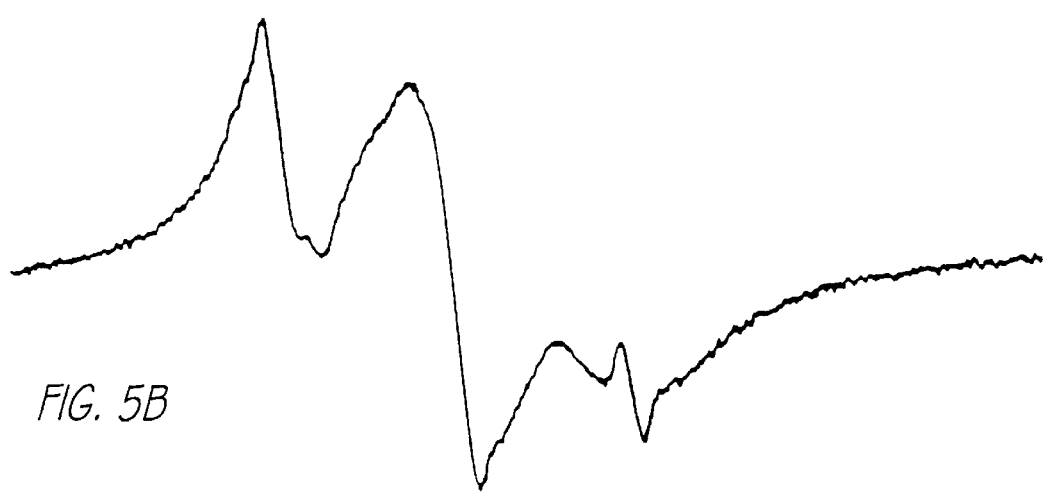
Figure 5C:
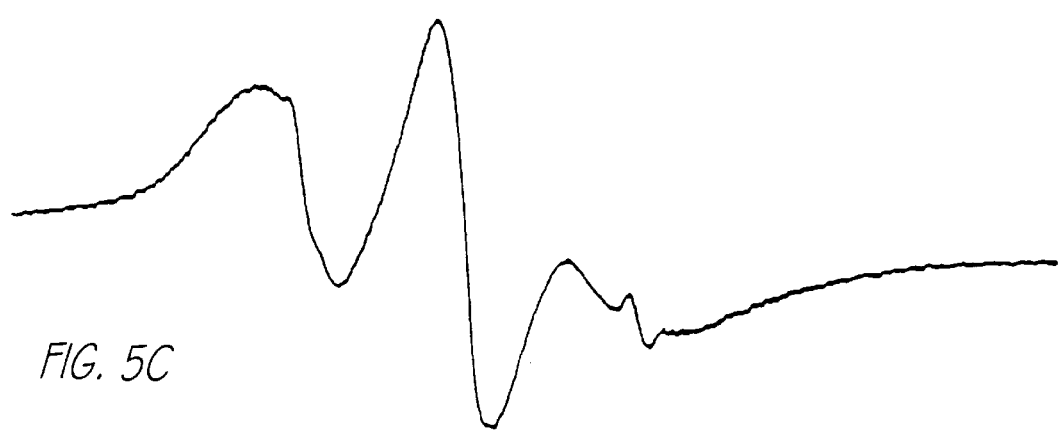

Also, any purified hemoglobin may be encapsulated with a liposome comprised of nitroxide-labelled fatty acids (e.g., 7-DOXYL-stearate, 12-DOXYL-stearic acid, and 16-DOXYL-stearate), cholestane, an analogue of cholesterol (e.g., 3-DOXYL-cholestane), or phospholipid (e.g., 12-DOXYL-stearate-labelled phosphatidylcholine). The preparation of hemoglobin encapsulated in a liposome comprised of 3-DOXYL-cholestane labelled may be prepared by a method analogous to that described in Tabushi et. al., (J. Am. Chem. Soc. 106:219 (1984)). A 5 ml chloroform solution containing lipid compositions, including DOXYL labelled stearic acid and/or cholestane, as specified below were first dried in a stream of nitrogen to remove the solvent. Next, the residues were dried in vacuo and the resulting film was suspended in 2 ml of hemoglobin (24 g/dl) in a Lactated Ringers solution. The lipid concentration in the dispersion is 100 mM. The liposome encapsulated hemoglobin is then rotated and incubated preferably at 37° C. until all lipids are dispersed to form multilamellar vesicles. The resulting solution containing multilamellar liposome encapsulated hemoglobin and free unencapsulated hemoglobin is then forced through a microfluidizer to form 0.2 micron liposomes according to the procedure of Cook et.al. (See U.S. Pat. No. 4,533,254). The molar ratio of dipalmitoyl phosphatidylcoline:cholesterol:dipalmitidyl phosphatidic acid:3-DOXYL-cholestane in the liposome is 0.5:0.4:0.02:0.07. The resonance spectrum of the resulting 3-DOXYL-cholestane labelled liposome-encapsulated hemoglobin is shown in FIG. 5A. In this configuration, the nitroxide is intercalated into the liposome membrane and can be found at both the inner and outer surface of the lipid bilayer water interface. Substituting the 3-DOXYL-cholestane with 16-DOXYL-stearic acid in the lipid composition shown in FIG. 5A results in an electron resonance spectrum shown in FIG. 5B. The mobility of the nitroxide as reflected from the resonance spectrum is consistent with the interpretation that the DOXYL-moiety of the stearic acid is located predominately in the hydrophobic interior of the lipid bilayer. With the addition of both the 3-DOXYL-cholestane and 16-DOXYL-stearate to the lipid composition at the same molar ratio, the resonance spectrum of the double nitroxide labelled liposome encapsulated hemoglobin is shown in FIG. 5C. The resonance spectrum of FIG. 5C is a composite of FIGS. 5A and 5B because the nitroxides in this embodiment are located at both the membrane-water interface and its hydrophobic lipid bilayer interior. By placing the nitroxide in both locations, this embodiment provides the oxygen detoxification function at both the lipid bilayer hydrophobic interior and the membrane-water interface thus providing the added benefit of an additional reserve of oxygen-detoxification capacity for the encapsulated hemoglobin.

V. Fifth Preferred Embodiment—Nitroxide-Labelled Conjugated Hemoglobin

A physiologically compatible solution of conjugated hemoglobin is produced by forming a conjugate of hemoglobin and a biocompatible macromolecule used as a plasma expander. Plasma expanders, such as dextran (Dx), polyoxyethylene (POE), hydroxylethyl starch (HES), are used to increase the circulation half life of hemoglobin in the body. In this state, the hemoglobin molecules together with the biocompatible macromolecule are collectively referred to as a hemoglobin conjugate. There are a number of convenient methods to incorporate a nitroxide into a hemoglobin conjugate. For example, one may simply substitute the hemoglobin to be conjugated with a nitroxide-labelled hemoglobin such as TEMPO labelled DBBF-Hb. This can be accomplished by substituting hemoglobin or pyridoxylated hemoglobin with 3-maleimido-PROXYL-DBBF-Hb or 4-(2-bromoacetamido)-TEMPO-DBBF-Hb in the preparation of conjugated hemoglobin.

Figure 6:
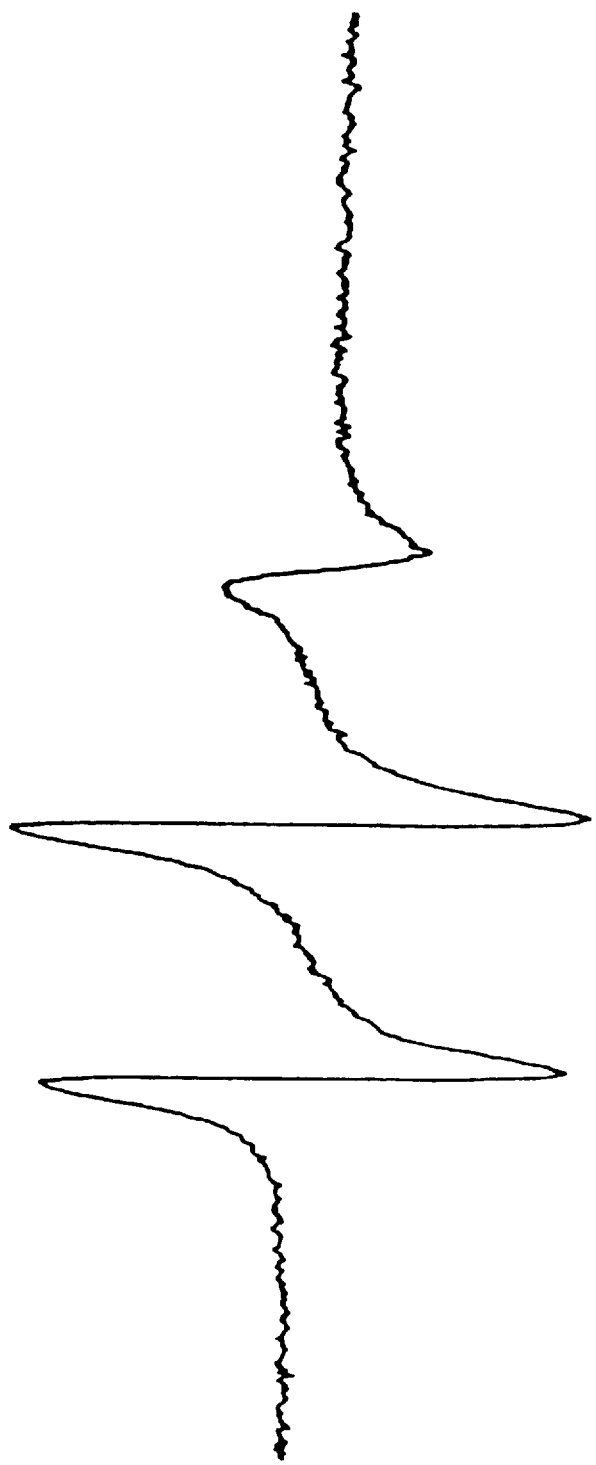
FIG. 6 is the electron spin resonance spectrum of nitroxide-labelled hemoglobin labelled with 4-amino-TEMPO and conjugated with dextran.

4-Amino-TEMPO labelled dextran conjugated hemoglobin is prepared in accord with the procedure described by Tam et. al. (Proc. Natl. Acad. Sci., 73:2128 (1976)). Initially, an 8% hemoglobin solution in 0.15M NaCl and 5 mM phosphate buffer, pH 7.4 is conjugated to periodate-oxidized dextran to form a Schiff-base intermediate. Twenty molar equivalents of 4-amino-TEMPO is added to hemoglobin to form the Schiff-base between the nitroxide and the remaining reactive aldehyde groups on the dextran. After a 30 minute of incubation at 4° C., a 50 molar equivalent of dimethylamine borane in water is added. The solution is incubated for a further 2 hours at 4° C. Afterwards, the solution is dialyzed, reconstituted with Lactate Ringers buffer and sterile filtered with Filtron membrane filtration units (Filtron Technology Co.). The electron spin resonance spectrum of the 4-amino-TEMPO labelled dextran-conjugated hemoglobin is a sharp asymmetric triplet reflecting a high degree of motional freedom (See FIG. 6). The increased mobility of the TEMPO covalently attached to the Dextran is consistent with the nitroxide linked to a flexible polysaccharide dextran chain as compared to that of a tightly folded hemoglobin molecule (See FIGS. 3A and 3B). Thus, resonance spectrum in FIG. 6 demonstrates that a novel nitroxide labelled dextran conjugated hemoglobin has been prepared.

Although the invention has been illustrated by the specific embodiments described above, due to variety of forms of physiologically compatible hemoglobin and the structural diversity of the stable nitroxide-free radicals, a number of variations on the above embodiments are possible without departing from the basic spirit of the invention as described by the following claims.

I claim as follows:

1. An apparatus for intravenous administration of solutions of cell-free hemoglobin comprising:

a solution of cell-free hemoglobin in fluid connection with a housing having an inlet and an outlet through which said solution of cell-free hemoglobin flows, and a nitroxide bound to a matrix contained within the housing.

2. The apparatus of claim 1 wherein the nitroxide has the structure

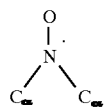

where the alpha carbon atoms are completely substituted such that the stability of the free radical is preserved.

3. The apparatus of claim 2 wherein the nitroxide has the structure

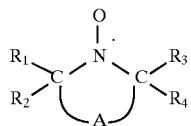

where $R_1$–$R_4$ are alkyl groups of 1–4 carbon atoms and A is the remaining members of a 5-membered ring.

4. The apparatus of claim 2 wherein the nitroxide is 2,2,5,5-tetramethylpyrrolidine-N-oxyl.

5. The apparatus of claim 2 wherein the nitroxide has the structure

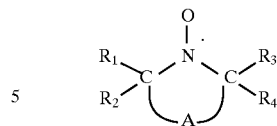

where $R_1$–$R_4$ are alkyl groups of 1–4 carbon atoms and A is the remaining members of a 6-membered ring.

6. The apparatus of claims 1 or 2 wherein the nitroxide is 2,2,6,6-tetramethylpiperidine-N-oxyl.

7. The apparatus of claims 1, 2, 3, 4, or 5 wherein the matrix is an agarose gel.

\* \* \* \* \*